United States Patent [19]

Block

[11] Patent Number: 5,936,001
[45] Date of Patent: Aug. 10, 1999

[54] DISINFECTING AND STERILIZING CONCENTRATE CONTAINING AN AROMATIC DIALDEHYDE AND A NEUTRAL PH BUFFERING SYSTEM

[75] Inventor: Phillip A. Block, Double Oak, Tex.

[73] Assignee: Ethicon, Inc.

[21] Appl. No.: 09/010,351

[22] Filed: Jan. 21, 1998

[51] Int. Cl.⁶ ..................................... A01N 35/00
[52] U.S. Cl. ........................... 514/698; 514/699
[58] Field of Search ................. 514/698, 697, 514/699, 702, 705

[56] References Cited

U.S. PATENT DOCUMENTS

| | | |
|---|---|---|
| 4,847,304 | 7/1989 | Bruckner et al. .............. 514/699 |
| 4,851,449 | 7/1989 | Bruckner et al. . |
| 4,971,999 | 11/1990 | Bruckner et al. . |
| 5,128,051 | 7/1992 | Theis et al. . |

*Primary Examiner*—Jose' G. Dees
*Assistant Examiner*—Alton Pryor
*Attorney, Agent, or Firm*—Andy Arismendi, Jr.; Kevin R. Hansbro

[57] ABSTRACT

A disinfecting and sterilizing concentrate containing an aromatic dialdehyde and a neutral pH buffering system is provided. Aromatic dialdehyde concentrations of greater than 5 w/w% are achieved while maintaining the stability of the buffering system. A method and a kit for preparing a disinfecting and sterilizing concentrate is also provided.

24 Claims, No Drawings

DISINFECTING AND STERILIZING CONCENTRATE CONTAINING AN AROMATIC DIALDEHYDE AND A NEUTRAL PH BUFFERING SYSTEM

BACKGROUND OF THE INVENTION

1. Field of Invention

The present invention relates to disinfecting and sterilizing solutions, and more particularly to a disinfecting and sterilizing concentrate containing an aromatic dialdehyde and a neutral pH buffering system.

2. Description of Prior Art

Aromatic dialdehyde disinfecting and sterilizing solutions are well known in the art. Aromatic dialdehyde solutions have bacteriostatic and fungistatic activity. They are useful for disinfecting or sterilizing medical devices or environmental surfaces. Unfortunately, present aromatic dialdehyde solutions limit the concentration of the aromatic solution to less than or equal to 5 w/w% of the total solution because aromatic dialdehydes have limited aqueous solubility. While water-miscible solvents may increase the solubility of aromatic dialdehyde, the solvents adversely affect the buffering systems of aromatic dialdehyde disinfecting and sterilizing solutions.

Bruckner et al. in U.S. Pat. No. 4,971,999, discuss ortho-phthalaldehyde as the active ingredient in an aromatic dialdehyde disinfecting and sterilizing solution. U.S. Pat. No. 4,971,999 is incorporated herein by reference. They discuss "in-use solutions" and more concentrated solutions. An "in-use solution" contains an effective amount of the active aromatic dialdehyde ingredient and is a solution which is sufficiently dilute for ordinary disinfecting and sterilizing purposes.

Bruckner et al. observe that for "in-use solutions," ortho-phthalaldehyde is normally present in amounts between 0.025 w/w% and 1 w/w%. They also observe that higher concentrations, e.g., up to 2 w/w%, can be used but that the preferred concentration is 0.05 w/w% to 0.5 w/w%. They further observe that higher concentrations may be used for shipping the solution to the point of use and the solution can then be diluted with water to the desired "in-use solution" concentration.

In any event, they note that the limit on the amount of ortho-phthalaldehyde used in the concentrate solution is a function of the solubility of the aromatic dialdehyde in water, which is about 5 w/w%. Bruckner et al. indicate that the concentration may be increased above the 5 w/w% level with the addition of water-miscible solvents. They specifically state that suitable solvents include methanol, ethanol, isopropanol, glycols, tetrahydrofuran, dimethyl sulfoxide, and dioxane. But, Bruckner et al. do not discuss or address any adverse affects caused by the additional solvents. There are some adverse affects.

Bruckner et al. observe that an alkalinating or acidifying salt can be used in the compositions (solutions) as a buffer to maintain a desired composition pH during storage and use. Bruckner specifically discloses an alkali metal carbonate or bicarbonate, e.g., sodium bicarbonate or potassium bicarbonate, or phosphate as a buffering salt. They note that the buffer may be an organic carboxylate salt such as sodium citrate, sodium acetate, potassium hydrogen phthalate, potassium citrate, or potassium acetate, or an inorganic borate salt such as potassium or sodium borate.

While Bruckner et al. contend that the disinfecting properties of the composition are not pH dependent, they do note that the sporicidal activity of an aromatic dialdehyde solution is somewhat pH dependent. They specifically observe this pH dependency at low aromatic aldehyde concentrations (e.g., 0.5 w/w% or less for phthaladehyde). They report that the optimal pH range for sporicidal activity is between 6 and 8 and thereby underscore the importance of buffering.

Moreover, the pH range from about 6 up to about 8 is preferred to ensure materials compatibility of certain medical instruments or utensils. Certain medical instruments or utensils are prepared from materials such as anodized aluminum, carbon steel, and rubber. These materials are chemically incompatible with environments outside the pH range from about 6 up to about 8. Therefore, to prevent harm to medical instruments or utensils prepared from these materials, a buffering system is required to maintain a pH in the range from about 6 up to about 8.

Unfortunately, the concentration of water-miscible solvents required to increase the concentration of the aromatic dialdehyde above 5 w/w% are generally incompatible with the buffering system of the aromatic dialdehyde solutions. That is, as the concentration of the aromatic dialdehyde is increased by the addition of water-miscible solvents, the physical stability of the buffering system is diminished. This physical instability is particularly apparent with phosphate buffering systems. To achieve and maintain the desired pH range from about 6 to about 8, the concentration of the buffering system must be increased as the concentration of aromatic dialdehyde is increased. Accordingly, there is a need to increase the concentration of the aromatic dialdehyde and the concentration of the pH buffering system while maintaining the physical stability of the pH buffering system. In other words, there is a need to stabilize the buffering systems of concentrated aromatic dialdehyde solutions against the water-miscible solvents used to increase the concentration of the aromatic dialdehyde. Throughout the entire process, there is, of course, a need to ensure the chemical stability of the aromatic dialdehyde.

SUMMARY OF THE INVENTION

According to the present invention, a disinfecting and sterilizing concentrate containing an aromatic dialdehyde and a neutral pH buffering system is provided. More specifically, there is provided a disinfecting and sterilizing concentrate comprising an aromatic dialdehyde present in a concentration greater than 5 w/w%, a water miscible solvent, and a pH buffering salt. Concentrations of greater than 5 w/w% are achieved while maintaining the physical stability of the pH buffering system. A method and a kit for preparing a disinfecting and sterilizing concentrate is also provided. Further, a reduction of the amount of waste materials is achieved by reducing the amount of packaging required to deliver aromatic dialdehyde disinfecting and sterilizing solutions.

DESCRIPTION OF THE INVENTION

A disinfecting and sterilizing concentrate comprising an aromatic dialdehyde present in a concentration greater than 5 w/w%, a water miscible solvent, and a pH buffering salt is provided. The concentrate may additionally contain a stabilizer, water, and minor ingredients. The water-miscible solvent increases the solubility of the aromatic dialdehyde. The pH buffering salt maintains the pH of the "in use solution." The stabilizer protects the pH buffering salt from the harmful effects of the water-miscible solvent.

The aromatic dialdehydes useful in the present invention preferably have the formula:

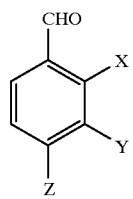

and are commonly called:
ortho-phthalaldehyde, where X is CHO and Y and Z are H, isophthalaldehyde, where Y is CHO and X and Z are H, and terephthalaldehyde, where Z is CHO and X and Y are H.

The preferred aromatic dialdehyde is ortho-phthalaldehyde because of its good solubility in water and disinfecting and sterilizing activity. The aromatic dialdehyde is present in an "in-use solution" concentration in an amount ranging from about 0.025 w/w% and 1 w/w%. A preferred concentration ranges from about 0.05 w/w% to about 0.6 w/w%.

Suitable water-miscible solvents include solvents having either a hydroxy or carbonyl group (such as ethanol, methanol, 1,4-butanediol, ethylene glycol, propylene glycol, isopropanol, acetone, and polyols), dimethylsulfoxide, dioxane, and tetrahydrofuran. Solvents with lower human toxicity are preferable and include ethanol, 1,4-butanediol, and propylene glycol.

Suitable buffering salts for maintaining a pH range from about 6 to about 8 include boric acid/sodium borate, maleic acid/sodium maleate, monobasic phosphate/dibasic phosphate, and citric acid/sodium citrate. Other buffering salts can achieve the desired pH range, but buffering salts with lower human toxicity are preferable. For example, cacodylate and sodium barbital are buffering salts that can achieve the desired pH, but these salts would not prove useful because they pose human toxicity problems. The identified buffering salts are preferred in this order: (1) monobasic phosphate/dibasic phosphate, (2) citric acid/sodium citrate, (3) boric acid/sodium borate, and (4) maleic acid/sodium maleate.

It should be noted that aromatic dialdehydes are also incompatible with buffering systems having primary or secondary amines. Notably, aromatic dialdehydes cross-link primary or secondary amine buffering systems and thereby reduce the concentration of both the aromatic dialdehyde and the buffering systems. For example, tris (hydroxymethyl) aminomethane and 2-amino-2-methyl-1,3-propanediol are amines that can cross-link in the presence of an aromatic dialdehyde.

Suitable stabilizers to protect the buffering salts against the adverse effects of the water-miscible solvents include polyols (such as glycerol and sorbitol) and propylene carbonate. The physical stability of the buffering salt is defined as no formation of precipitates or phase separation of the buffered solution at 4° C. for a minimum of 2 weeks and is determined by visual inspection. The chemical stability of the aromatic dialdehyde is defined as no loss of the aromatic dialdehyde in excess of 15% of the total amount initially present at 40° C. for a minimum of sixty (60) days and is determined by high performance liquid chromatography.

Suitable minor ingredients include dyes, chelants [e.g., ethylenediaminetetraacetic acid (EDTA), citric acid], and builders [e.g., sodium tripolyphosphate (STPP), other phosphonates]. The use of minor ingredients is well known to those of ordinary skill in the art and does not affect the active ingredients of the solutions or solutions' performance.

The relationship between the solvent/stabilizer and the buffering salts affects the choice of buffering salt. Notably, phosphate buffering systems are more sensitive to alcohol (solvent) concentrations as compared to borate or maleate buffering systems. Because maleate buffering systems are not as sensitive to alcohol concentrations as other buffering systems, lower concentrations of stabilizers are appropriate. In fact, a stabilizer may be an unnecessary ingredient for certain concentrate formulations containing a maleate buffering systems. It should also be noted that some buffering systems are insoluble in alcohols and diols, for example, phosphate buffering systems are insoluble in alcohol.

In an embodiment of the invention, a formulation of the concentrate is represented as:

| Ingredient | Weight Percent (w/w %) |
| --- | --- |
| Aromatic Dialdehyde | 5–30 |
| Solvent | 1–60 |
| Buffer Salts | 0.5–25 |
| Stabilizer | 0–50 |
| Water & Minor Ingredients | remainder |

In a preferred embodiment of the invention, a formulation of the concentrate is represented as:

| Ingredient | Weight Percent (w/w %) |
| --- | --- |
| Aromatic Dialdehyde | 5–25 |
| Solvent | 5–50 |
| Buffer Salts | 1–20 |
| Stabilizer | 0–45 |
| Water & Minor Ingredients | remainder |

In a more preferred embodiment of the invention, a formulation of the concentrate is represented as:

| Ingredient | Weight Percent (w/w %) |
| --- | --- |
| Aromatic Dialdehyde | 10–20 |
| Solvent | 10–45 |
| Buffer Salts | 1–15 |
| Stabilizer | 0–40 |
| Water & Minor Ingredients | remainder |

The order of addition affects the formulation time. Preferably and to reduce formulation time, the water-miscible solvent and the water are first mixed together. Next, the stabilizer is admixed. Next, the buffer salt is admixed. Next, the aromatic dialdehyde is admixed to the solution. Finally, the minor ingredients are admixed. The order of addition affects formulation time for at least two reasons. If the aromatic dialdehyde is added directly to the water, the aromatic dialdehyde becomes hydrated. As a hydrate, the aromatic dialdehyde dissolves more slowly in the water-miscible solvent. Accordingly, it is desirable to avoid hydration of the aromatic dialdehyde. Because the rate of dissolution and the stability of the aromatic dialdehyde is somewhat pH dependent, addition of the aromatic dialdehyde should preferably follow the addition of the buffering salt. Notably, the aromatic dialdehyde dissolves more slower in low pH solutions than it does in neutral pH solutions. Also, if dissolved into solutions having a pH above neutral, the aromatic dialdehyde is more likely to polymerize than it is in solutions having a neutral pH. Additionally, the boric acid buffering system will dissolve more quickly in the stabilizer glycerol if the glycerol is heated. However, when using volatile solvents, such as ethanol, the heating of the formulation is controlled to minimize evaporation losses.

AN ALTERNATE EMBODIMENT

In an alternate embodiment, a kit for preparing a disinfecting and sterilizing concentrate is provided. In the kit, the concentrated aromatic dialdehyde and the buffering system are maintained as two distinct solutions, as they are separately packaged, for example, in a single split-chamber bottle. The split-chamber bottle provides for a single dosing method. In this embodiment, the second solution may be physically or chemically incompatible with the first solution. This embodiment is particularly useful with phosphate buffering systems because phosphate buffering systems are particularly sensitive to alcohol (solvent) concentrations.

In this alternate embodiment, a formulation for the kit is represented as:

| Solution for Chamber 1 | | Solution for Chamber 2 | |
|---|---|---|---|
| Ingredient | Weight Percent* | Ingredient | Weight Percent* |
| Aromatic Dialdehyde | 5–60 | Buffering Salt | 1–50 |
| Solvent | 2–70 | Water & Minor | remainder |
| Water | remainder | Ingredients | |

*Weight percent is weight-by-weight percent (w/w %).

In a preferred alternate embodiment, a formulation for the kit is represented as:

| Solution for Chamber 1 | | Solution for Chamber 2 | |
|---|---|---|---|
| Ingredient | Weight Percent | Ingredient | Weight Percent |
| Aromatic Dialdehyde | 10–50 | Buffering Salt | 2–40 |
| Solvent | 10–50 | Water & Minor | remainder |
| Water | remainder | Ingredients | |

In a more preferred alternate embodiment, a formulation for the kit is represented as:

| Solution for Chamber 1 | | Solution for Chamber 2 | |
|---|---|---|---|
| Ingredient | Weight Percent | Ingredient | Weight Percent |
| Aromatic Dialdehyde | 20–40 | Buffering Salt | 2–30 |
| Solvent | 20–50 | Water & Minor | remainder |
| Water | remainder | Ingredients | |

In the alternate embodiment, the minor ingredients may be added to Solution 1, Solution 2, or both. Adding the minor ingredients to Solution 2 is preferable because it avoids any potential interaction between the minor ingredients and the aromatic dialdehyde of Solution 1. Also, a stabilizer is unnecessary in the alternate embodiment because the buffering system and the water-miscible solvent are not combined until just prior to use and at "in-use solution" concentrations. Moreover, Solution 1 and Solution 2 of the kit may be combined in various ratios, for example, 3:1, 2:1, 1:1, 1:2, and 1:3, respectively. The preferred ratio is 1:1.

EXAMPLES

The following formulations exemplify the more preferred embodiment and the more preferred alternate embodiment. The formulations are at 24X concentrates, where X is the "in-use solution" concentration. It is understood that the following examples are provided to further illustrate the invention. They do not in anyway limit the scope of the present invention.

EXAMPLE #1

In this example, a concentrate having the following formulation was prepared:

| Ingredient | Weight Percent (w/w %) |
|---|---|
| ortho-phthalaldehyde | 11.5 |
| ethanol | 19.5 |
| boric acid | 5.8 |
| borax | 3.5 |
| glycerol | 39.0 |
| water | 19.5 |
| minor ingredients | 1.2 |

This formulation was prepared by first mixing the ethanol and water together. Next, the glycerol was added. The composition was then heated because the borate buffering system dissolves more quickly at higher temperatures. The boric acid and borax ingredients were then added. The resulting composition was then cooled to prevent evaporation of the ethanol. The ortho-phthalaldehyde was then added to the mixture. The minor ingredients including 0.5 w/w% of a 1% dye in water solution, 0.5 w/w% of 1% calcium sequestrant (EDTA) in water solution, and 0.2 w/w% of a copper sequestrant (benzotriazole) were then added.

Evidence of pH Buffering

An "in-use solution" of the concentrate was prepared by diluting the concentrate 24 times. The "in-use solution" has a pH of 7.5. The solution's pH decreases by only 0.3 units when the "in-use solution" is diluted by half with water. The solution's pH decreases by only 0.3 units per mL of 0.1 N HCl added to the "in-use solution."

EXAMPLE #2

In this example, a concentrate having the following formulation was prepared:

| Ingredient | Weight Percent (w/w %) |
|---|---|
| ortho-phthalaldehyde | 11.0 |
| 1,4-butanediol | 37.6 |
| maleic acid | 7.5 |
| sodium hydroxide | 5.3 |
| water | 37.6 |
| minor ingredients | 1.0 |

This formulation was prepared by first adding the sodium hydroxide to the water. The resulting solution was cooled. Next, the maleic acid was added. The solution was again cooled. Next, the 1,4-butanediol was admixed. Then, the ortho-phthalaldehyde was admixed. The minor ingredients including 0.5 w/w% of a 1 % dye in water solution and 0.5 w/w% of 1 % calcium sequestrant (namely, EDTA) in water solution were finally added.

Because this concentrate contained a maleate buffering system, the buffering system did not require a stabilizer against the water-miscible solvent, 1,4-butanediol. Maleate buffering systems are not particularly sensitive to solvent concentration up to 24X concentrates. If concentrates of 30X or greater are desired, a stabilizer is preferably added to protect the physical stability of the maleate buffering system.

Evidence of pH Buffering

An "in-use solution" of the concentrate was prepared by diluting the concentrate 24 times. The "in-use solution" has a pH of 7.2. The solution's pH decreases by only 0.1 units when the "in-use solution" is diluted by half with water. The solution's pH decreases by only 0.05 units per mL of 0.1 N HCl added to the "in-use solution."

EXAMPLE #3

Split-Chamber System

In this example, a kit is exemplified by the following formulation. A single split-chamber bottle is used. The concentrated aromatic dialdehyde solution is in Chamber No. 1, and the buffering system is in Chamber No. 2.

| Solution for Chamber 1 | | Solution for Chamber 2 | |
| --- | --- | --- | --- |
| Ingredient | Weight Percent | Ingredient | Weight Percent |
| ortho-phthalaldehyde | 25 | sodium monobasic phosphate | 6 |
| ethanol | 30 | sodium dibasic phosphate | 18 |
| distilled water | 45 | distilled water | 75 |
| | | minor ingredients | 1 |

Solution 1 of this formulation was prepared by adding the ethanol to the distilled water. Next, the ortho-phthalaldehyde was added to ethanol/water mixture.

Solution 2 was prepared by first heating the distilled water because the phosphate salt dissolves more quickly in heated water than it does in cool water. The sodium monobasic phosphate and sodium dibasic phosphate ingredients were then added to the heated water. The minor ingredients were then added. The minor ingredients included 0.5 w/w% of a 1% dye in water solution and 0.5 w/w% of 1% calcium sequestrant (EDTA) in water solution.

EXAMPLE #4

Physical And Chemical Stability of Exemplified Formulations

In this example, the formulations as prepared in Examples 1 and 2 and the kit as prepared in Example 3 were tested. Physical stability is defined as no formation of precipitates or phase separation of the solution, as determined visually. Chemical stability of the aromatic dialdehyde is determined by high performance liquid chromatography.

Both formulations of Examples 1 and 2 showed physical and chemical stability at 40° C. for a minimum of sixty (60) days. That is, after 60 days, neither formulation showed the formation of a precipitate or phase separation nor a loss of the aromatic dialdehyde in excess of 15% of the total amount initially present.

The kit of Example 3 showed physical and chemical stability at 40° C. for a minimum of thirty (30) days. After 30 days, the kit did show the formation of a precipitate or phase separation nor a loss of the aromatic dialdehyde in excess of 15% of the total amount initially present The kit was not tested beyond thirty days. The kit is expected to have continued physical and chemical stability beyond sixty (60) days because the solvent and buffering systems are maintained in separate solutions.

At 4° C., both formulations of Examples 1 and 2 and the kit of Example 3 demonstrated physical and chemical stability in excess of two (2) weeks.

The preferred embodiments and examples are given to illustrate the scope and spirit of the present invention. The embodiments and examples herein will make apparent to those skilled in the art other embodiments and examples. These other embodiments and examples are within the scope of the present invention. Thus, the scope of the invention should be determined by the appended claims and their legal equivalents, rather than by the examples given herein.

What is claimed is:

1. A disinfecting and sterilizing concentrate comprising:
   (a) an aromatic dialdehyde present in a concentration of at least 10" w/w%,
   (b) a water miscible solvent, and
   (c) a buffering salt.

2. The disinfecting and sterilizing concentrate of claim 1, wherein
   (a) the aromatic dialdehyde is selected from the group consisting of ortho-phthalaldehyde, isophthalaldehyde, and terephthalaldehyde.

3. The disinfecting and sterilizing concentrate of claim 1, wherein
   (b) the solvent is selected from the group consisting of ethanol, methanol, 1,4-butanediol, ethylene glycol, propylene glycol, tetrahydrofuran, isopropanol, polyols, dimethylsulfoxide, and dioxane.

4. The disinfecting and sterilizing concentrate of claim 1, wherein
   (c) the buffering salt is selected from the group consisting of boric acid/sodium borate, maleic acid/sodium maleate, monobasic phosphate/dibasic phosphate, and citric acid/sodium citrate.

5. The disinfecting and sterilizing concentrate of claim 1, further comprising
   (d) a stabilizer.

6. The disinfecting and sterilizing concentrate of claim 5, wherein
   (d) the stabilizer is selected from the group consisting of glycerol, sorbitol, and propylene carbonate.

7. The disinfecting and sterilizing concentrate of claim 1, further comprising
   (e) at least one minor ingredient selected from the group consisting of dyes, chelants, and builders.

8. The disinfecting and sterilizing concentrate of claim 5, further comprising
   (e) at least one minor ingredient selected from the group consisting of dyes, chelants, and builders.

9. The disinfecting and sterilizing concentrate of claim 1, wherein
   (a) the aromatic dialdehyde is present in a concentration of at least 10" w/w % up to about 30 w/w%,
   (b) the solvent present in a concentration ranging from about 1 w/w% to about 60 w/w%, and
   (c) the buffering salt is present in a concentration ranging from about 0.5 w/w% to about 25 w/w%.

10. The disinfecting and sterilizing concentrate of claim 9, further comprising
    (d) a stabilizer present in a concentration up to about 50 w/w %.

11. The disinfecting and sterilizing concentrate of claim 1, wherein
    (a) the aromatic dialdehyde is present in a concentration of at least 10" w/w% up to about 25 w/w%,
    (b) the solvent is present in a concentration ranging from about 5 w/w% to about 50 w/w%, and (c) the buffering salt is present in a concentration ranging from about 1 w/w % to about 20 w/w%.

12. The disinfecting and sterilizing concentrate of claim 11, further comprising
   (d) a stabilizer present in a concentration up to about 45 w/w%.

13. The disinfecting and sterilizing concentrate of claim 1 wherein
   (a) the aromatic dialdehyde is present in a concentration ranging from at least 10 w/w% to about 20 w/w%,
   (b) the solvent is present in a concentration ranging from about 10 w/w% to about 45 w/w%, and
   (c) the buffering salt is present in a concentration ranging from about 1 w/w % to about 15 w/w%.

14. The disinfecting and sterilizing concentrate of claim 13, further comprising
   (d) a stabilizer present in a concentration up to 40 w/w%.

15. A method for making a disinfecting and sterilizing concentrate comprising:
   (i) mixing an amount of an aromatic dialdehyde of at least 10" w/w% with a water-miscible solvent and
   (ii) admixing a buffering salt.

16. The method of claim 15, further comprising
   (iii) admixing a stabilizer.

17. The method of claim 15, further comprising
   (iv) admixing at least one minor ingredient selected from the group consisting of dyes, chelants, and builders.

18. A disinfecting and sterilizing concentrate prepared in accordance with the method of claim 15.

19. A disinfecting and sterilizing concentrate prepared in accordance with the method of claim 16.

20. A disinfecting and sterilizing concentrate prepared in accordance with the method of claim 17.

21. A kit for preparing a disinfecting and sterilizing concentrate comprising
   (a) a first solution having
      (i) an aromatic dialdehyde present in a concentration of at least 10" w/w% and
      (ii) a water-miscible solvent, and
   (b) a second solution having
      (iii) at least a buffering salt.

22. The kit of claim 21, wherein
   (i) the aromatic dialdehyde of the first solution is present in a concentration of at least 10" w/w% up to about 60 w/w%,
   (ii) the solvent of the first solution is present in a concentration ranging from about 2 w/w% to about 70 w/w%, and
   (iii) the buffering salt of the second solution is present in a concentration ranging from about 1 w/w% to about 50 w/w%.

23. The kit of claim 21, wherein
   (i) the aromatic dialdehyde of the first solution is present in a concentration ranging from at least 10 w/w% to about 50 w/w%,
   (ii) the solvent of the first solution is present in a concentration ranging from about 10 w/w% to about 50 w/w%, and
   (iii) the buffering salt of the second solution is present in a concentration ranging from about 2 w/w% to about 40 w/w%.

24. The kit of claim 21, wherein
   (i) the aromatic dialdehyde of the first solution is present in a concentration ranging from about 20 w/w% to at least 40 w/w%,
   (ii) the solvent of the first solution is present in a concentration ranging from about 20 w/w% to about 50 w/w%, and
   (iii) the buffering salt of the second solution is present in a concentration ranging from about 2 w/w% to about 30 w/w%.

* * * * *